United States Patent [19]

Chiu

[11] Patent Number: 4,873,370
[45] Date of Patent: Oct. 10, 1989

[54] ALKYLENE DIAMINES FOR USE IN FRICTION AND WEAR REDUCING COMPOSITIONS

[75] Inventor: I-Ching Chiu, Houston, Tex.

[73] Assignee: Pennzoil Products Company, Houston, Tex.

[21] Appl. No.: 21,316

[22] Filed: Mar. 3, 1987

[51] Int. Cl.⁴ .................. C07C 61/16; C10M 105/08
[52] U.S. Cl. .................................. 564/500; 564/503; 252/50; 252/51; 252/3; 252/51.5 R
[58] Field of Search ................. 564/500, 503; 252/50, 252/51, 51.5 R

[56] References Cited

U.S. PATENT DOCUMENTS 2,856,363 10/1958 Brennan .............................. 564/503
3,952,060 4/1976 Huber-Emden et al. ........... 564/503

FOREIGN PATENT DOCUMENTS 2530243 1/1977 Fed. Rep. of Germany .

OTHER PUBLICATIONS

Kanetani et al., *Nippon Kagaku Kaishi*, No. 12, pp. 1783–1791, (1983).
Izumi et al., *Chemical Abstracts*, vol. 84, No. 109029b, (1976).

*Primary Examiner*—Richard L. Raymond
*Assistant Examiner*—Raymond Covington
*Attorney, Agent, or Firm*—Lowe, Price, LeBlanc, Becker & Shur

[57] ABSTRACT

N,N-dialkyl-N'-(beta substituted) alkyl alkylene diamines of the formula

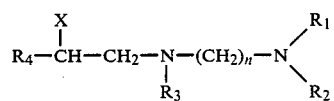

wherein $R_1$, $R_2$ and $R_3$ are $C_{1-4}$ hydrocarbon groups or H, but both $R_1$ and $R_2$ are not H, $R_4$ is a saturated or unsaturated $C_{14-24}$ hydrocarbon group, $n=1-4$ and X is OH or SH are adapted for use as friction and wear reducing additives in friction and wear reducing compositions.

10 Claims, No Drawings

ALKYLENE DIAMINES FOR USE IN FRICTION AND WEAR REDUCING COMPOSITIONS

FIELD OF THE INVENTION

The present invention relates to alkylene diamines, particularly N,N-dialkyl-N'-(beta substituted) alkyl alkylene diamines, and to methods for the production of the alkylene diamines. The present invention further relates to the use of the alkylene diamines as friction and wear reducing additives in friction and wear reducing compositions, particularly compositions including a lubricant.

BACKGROUND OF THE INVENTION

Significant energy losses in motor and engine operation are caused by metal to metal contact under normal or heavy loads, even when the metal surfaces are lubricated. Energy losses due to the metal to metal friction may be reduced by blending a friction modifier in the commonly used lubricants whereby fuel consumption by engines and motors may also be reduced.

Various organic amines are known for use in lubricants as dispersing, anti-friction, anti-wear, anti-rust and corrosion inhibiting additives. For example, the Horodysky et al U.S. Pat. Nos. 4,328,113, 4,537,694 and 4,549,975 disclose alkyl amines and alkyl diamines which are useful as friction reducing additives in lubricating oils. The Karn U.S. Pat. No. 4,266,945 and the Coupland et al U.S. Pat. No. 4,164,473 disclose diamine compounds also including molybdenum atoms, which compounds are also useful as anti-friction and anti-wear additives for lubricating oils. Additionally, the Chao et al U.S. Pat. No. 4,264,461 discloses hydrocracked lubricating oils which are stabilized against deterioration caused by light by the inclusion of substantially aliphatic diamine compounds. The DeVries et al U.S. Pat. No. 4,134,844 discloses the use of solid particle stabilizers such as long chain polyamines to improve the lubricating properties of oils. Canadian Pat. No. 1,025,594 discloses polyhydrocarbon compounds including a terminal alkenyl diamine group for use as a dispersant in oil and fuel compositions.

Additionally, the Coupland et al U.S. Pat. No. 4,250,045 discloses lubricating oils including a dimeramine derived from a dicarboxylic acid containing at least 12 carbon atoms, which oils exhibit anti-friction and fuel economy properties. The use of polypropylene or polyisobutylene substituted polyamines as detergents or dispersants in fuels and lubricating oils is disclosed in the Honnen et al U.S. Pat. No. 3,574,576 while the use of mono- or polyamines containing at least 12 carbon atoms as lubricants for non-ferrous metals is disclosed in the Latos U.S. Pat. No. 3,814,212. The use of a salt of an aromatic carboxylic acid and di-(n-octadecyl)amine as a pour point depressant in hydrocarbon oils is disclosed in the Gaydasch U.S. Pat. No. 3,846,481.

The use of polyamines including an unsaturated higher fatty acid derived group as corrosion inhibitors for metal surfaces is disclosed in the McCaleb et al U.S. Pat. No. 3,010,782 while the Gipson U.S. Pat. No. 3,954,873 discloses the use of hydroxyamines as corrosion inhibitors for metals.

Organic diamine compounds are also known for other uses. For example, the Scudi et al U.S. Pat. No. 2,739,986 discloses the use of N,N,N',N'-alkyl substituted ethylene diamines as antiviral agents while the Szabo et al U.S. Pat. No. 2,868,833 discloses the use of alkyl substituted alkylene diamines as bronchodilator and antihistaminic agents. The Ambelang U.S. Pat. No. 2,939,861 discloses the use of phenylene diamines as inhibiting agents in rubber compounds and the Mitchell U.S. Pat. No. 4,521,627 discloses the use of alkylene diamines to form alkali metal salts for use in isomerization reactions. The Japanese reference No. 49-34519 discloses the use of hydroxydiamines in asphalt compositions and the McDonald U.S. Pat. No. 4,321,271 discloses the use of hydroxyamines as growth promoters. Additionally, the Abend U.S. Pat. No. 4,281,201 discloses cationic emulsifiers comprising beta-hydroxy substituted amine compounds.

Thus, various amine compounds are known for improving properties of lubricating oils and compositions and for many other uses.

SUMMARY OF THE INVENTION

It is an object of the present invention to provide new organic amine compounds, particularly new alkylene diamine compounds, and methods for producing the compounds. It is an additional object of the present invention to provide novel friction and wear reducing additives for use in friction and wear reducing compositions. It is a specific object of the invention to provide novel alkylene diamine compounds for use as friction and wear reducing additives in lubricating compositions. Additionally, it is a related object of the invention to provide friction and wear reducing compositions including the alkylene diamines of the present invention.

These and additional objects and advantages are provided by the alkylene diamines according to the present invention which comprise N,N-dialkyl-N'-(beta substituted) alkyl alkylene diamines of the formula:

TABLE I

| | Four-Ball Friction Test | |
|---|---|---|
| Composition | Weight Percent Additive | Percent Reduction in Coefficient of Friction (20kg load,1800rpm,75° C.) |
| 1 | 1 | 50 |
| 2 | 1 | 43 |
| 3 | 1 | 43 |
| Comparative 1 | — | 0 |

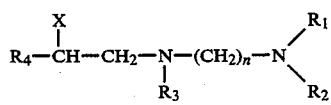

wherein $R_1$, $R_2$ and $R_3$ are $C_{1-4}$ hydrocarbon groups or H, but both $R_1$ and $R_2$ are not H, $R_4$ is a saturated or unsaturated $C_{14-24}$ hydrocarbon group, $n=1-4$ and X is OH or SH. These novel alkylene diamines are particularly adapted for use as friction and wear reducing additives, particularly in lubricant compositions. The present invention also includes methods for preparing the novel alkylene diamines by the reaction of an N,N-dialkyl alkylene diamine with an alpha-epoxyaliphatic or alpha-epithioaliphatic compound. The present invention further includes friction and wear reducing compositions comprising a lubricant and a friction and wear reducing additive comprising an alkylene diamine of the invention.

These and additional objects and advantages will be more fully understood in view of the following detailed description.

DETAILED DESCRIPTION

The N,N-dialkyl-N'-(beta substituted) alkyl alkylene diamines of the present invention are of the formula:

TABLE II

| | Optimal SRV Friction Coefficient Test Weight Percent | |
|---|---|---|
| Composition | Additive | Friction Coefficient |
| 4 | 2 | 0.120 |
| 5 | 2 | 0.127 |
| 6 | 2 | 0.133 |
| 7 | 2 | 0.143 |
| Comparative 2 | 2 | 0.144 |

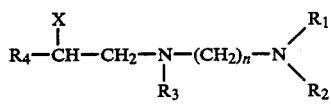

wherein $R_1$, $R_2$ and $R_3$ are $C_{1-4}$ hydrocarbon groups or H, but both $R_1$ and $R_2$ are not H, $R_4$ is a saturated or unsaturated $C_{14-24}$ hydrocarbon group, $n=1-4$ and X is OH or SH. In a specific embodiment, the alkylene diamines according to the invention are beta hydroxy substituted and are of the formula:

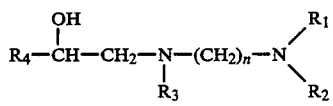

wherein $R_1$, $R_2$, $R_3$, $R_4$ and n are as defined above. In an additional specific embodiment of the invention, the alkylene diamines are beta thiol substituted and are of the formula:

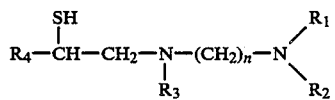

wherein $R_1$, $R_2$, $R_3$, $R_4$ and n are as defined above.

In preferred embodiments of the compounds according to the present invention, $n=1-3$ whereby the compounds comprise methylene diamines, ethylene diamines or propylene diamines, respectively. Additionally, while one of $R_1$ and $R_2$ may comprise hydrogen, it is preferred that both $R_1$ and $R_2$ are $C_{1-4}$ hydrocarbon groups. Additionally, it is preferred that when both $R_1$ and $R_2$ are $C_{1-4}$ hydrocarbon groups, they are the same hydrocarbon group.

The beta substituted alkyl alkylene diamines according to the present invention may be prepared by reacting an N,N-dialkyl alkylene diamine with a compound selected from the group consisting of alpha-epoxyaliphatics and alpha-epithioaliphatics. The N,N-dialkyl alkylene diamine should be of the formula $R_3HN-(CH_2)_n-NR_1R_2$ wherein $R_1$, $R_2$, $R_3$ and n are as previously defined. The aliphatic moiety included in the alpha-epoxyaliphatic and alpha-epithioaliphatic compounds comprises a saturated or unsaturated $C_{14-24}$ hydrocarbon group. The reaction may be affected with or without the presence of an acid catalyst as follows:

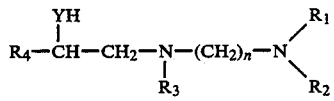

wherein Y is an oxygen or sulfur atom. In the ring opening reaction of the alpha-epoxyaliphatic compounds, the diamines generally attack from the less hindered side of the oxirane leading to the beta-hydroxy diamines. Only traces of the dimeric byproduct are formed as an impurity; however, to prevent the formation of the undesired byproduct, the reaction may be carried out with the molar ratio of diamine to epoxyaliphatic compound being from 2:1 to 3:1. The reaction may be completed within approximately two hours using a reflex temperature of from about 100° to 150° C. A similar reaction is affected using the epithioaliphatic compounds in place of the epoxyaliphatic compounds although lower reaction temperatures and longer reaction times may be employed.

The alpha epoxyaliphatic compounds may be obtained from the epoxidation of the corresponding alpha-olefin by known methods. These compounds are also commercially available. A mixture of $C_{14-24}$ epoxyaliphatic compounds may be used to produce the beta substituted alkyl alkylene diamines of the present invention. The alpha epithioaliphatic compounds may be obtained from the corresponding alpha epoxyaliphatic compounds by known methods using reactants such as KSCN, thiourea or triphenylphosphine sulfide.

Diamines of the formula $R_3NH(CH_2)_nNR_1R_2$ which are particularly useful for producing alkylene diamines in accordance with the present invention include N,N-dimethyl ethylene diamine, N,N-diethyl ethylene diamine, N,N-dibutyl ethylene diamine, N,N-dimethyl propylene diamine, N,N-diethyl propylene diamine, N,N-dibutyl propylene diamine, N,N,N'-trimethyl ethylene diamine, N,N,N'-triethyl ethylene diamine, N-methyl ethylene diamine, N-ethyl ethylene diamine, N,N'-dimethyl ethylene diamine, N,N'-dimethyl propylene diamine, and mixtures thereof.

The beta substituted alkyl alkylene diamines according to the present invention are particularly suitable for use as friction and wear reducing additives in friction and wear reducing compositions such as lubricants. Lubricant compositions including the beta substituted alkyl alkylene diamine compounds of the present invention exhibit reductions in friction and wear when used in engines, motors and other similar environments. The lubricant included in the compositions according to the present invention may be any natural or synthetic lubricant such as mineral oil or a fully formulated lubricating oil. The amount of the beta substituted alkyl alkylene diamine friction and wear reducing additive according to the present invention included in the lubricating composition will vary depending on the particular lubricant which is used. In most cases, friction and wear reducing properties will be provided when the beta substituted alkyl alkylene diamine of the present invention is included in the composition in an amount of from about 0.1 to about 10 weight percent. Preferably, the friction and wear reducing additive comprising the beta substituted alkyl alkylene diamine of the present invention is included in the friction and wear reducing compositions in an amount of from about 1 to about 5 weight percent.

The friction and wear reducing compositions according to the present invention comprising a lubricant and the friction and wear reducing additive may further include other additives such as detergents, viscosity index improvers, rust inhibitors, corrosion inhibitors, defoaming agents, pour-point depressants, dispersants, antioxidants and additional antiwear agents.

The following examples demonstrate the preparation of beta substituted alkyl alkylene diamines according to the present invention and the preparation and use of friction and wear reducing compositions according to the present invention.

EXAMPLE 1

This example demonstrates the preparation of N,N-diethyl-N'-(beta-hydroxy)octadecyl ethylene diamine. A suspension was prepared comprising alpha-epoxyoctadecane 85% (6.32 grams, 20 mmol), N,N-diethyl ethylene diamine (7.68 grams, 66 mmol) and a trace amount of p-toluenesulfonic acid catalyst. The suspension was heated to reflux under a nitrogen atmosphere. After refluxing for two hours, the excess diamine was distilled under reduced pressure. A portion of the residue was chromatographed on $SiO_2$ while the remainder was recrystallized from hexane to give 4.69 grams of a pale yellow solid having a melting point of 38°–41° C. The product was fully characterized by $^1H$, $^{13}C$ NMR, infrared and mass spectroscopic examinations.

EXAMPLE 2

In this example, the procedure of Example 1 was followed except that 4.08 grams (40 mmol) N,N-dimethyl propylene diamine were substituted for N,N-diethyl ethylene diamine whereby the product comprised N,N-dimethyl-N'-(beta-hydroxy)octadecyl propylene diamine.

EXAMPLE 3

In this example, the procedure of Example 1 was followed except that 3.44 grams (40 mmol) N,N'-dimethyl ethylene diamine was substituted for the N,N-diethyl ethylene diamine whereby the product comprised N-methyl-N'-(beta-hydroxy)octadecyl ethylene diamine.

EXAMPLE 4

This reaction demonstrates the preparation of N,N-diethyl-N'-(beta-thiol)octadecyl ethylene diamine. A reaction mixture was prepared comprising 1.42 grams (5 mmol) alpha-epithiolooctadecane, 1.16 grams (10 mmol) N,N-diethyl ethylene diamine and 3 drops of boron triflouride-etherate. The mixture was heated at 60° C. under a nitrogen atmosphere for 30 hours. The excess diamine was pumped off and the remaining residue was chromatographed to give the recited compound.

EXAMPLE 5

In this example, friction and wear reducing compositions were prepared using 100 neutral base oil. Compositions 1–3 were prepared comprising the neutral base oil and 1 weight percent of the compounds according to the present invention prepared in Examples 1–3, respectively. Comparative composition 1 comprised the neutral base oil without inclusion of a beta substituted alkyl alkylene diamine according to the present invention.

The compositions were tested according to the Four-Ball Friction Machine modified ASTM D-4172 method. The results are set forth in Table I and demonstrate that the compositions according to the present invention exhibited a 40 to 50% reduction in friction coefficients as compared to the comparative composition.

TABLE I

| | Four-Ball Friction Test | |
|---|---|---|
| Composition | Weight Percent Additive | Percent Reduction in Coefficient of Friction (20 kg load, 1800 rpm, 75° C.) |
| 1 | 1 | 50 |
| 2 | 1 | 43 |
| 3 | 1 | 43 |
| Comparative 1 | — | 0 |

EXAMPLE 6

In this example, additional friction and wear reducing compositions according to the present invention were prepared. Compositions 4–7 were prepared comprising a fully formulated 10W-30 oil and 2 weight percent of the compounds according to the present invention prepared in Examples 1–4, respectively. Comparative composition 2 was prepared comprising the fully formulated 10W-30 oil and 2 weight percent of a commercial friction modifier and antiwear agent, Keil Sul Perm 307 (a sulfur containing compound supplied by Keil Chemical Division, Ferro Corporation). The compositions were subjected to the Optimol SRV Friction Coefficient Test, a modified version of the SRV Wear Test, using a specimen ring (standard steel E 52100), 20×17×16.5 mm in size, to replace the standard ball on top of a disc. The test conditions included a load of 654N, a temperature of 100° C., a frequency of 40 Hz and a duration of 20 minutes. The results of the test are set forth in Table II. This example demonstrates that the compositions according to the present invention exhibit comparable or, as in most of the compositions, improved friction coefficients as compared with the comparative composition 2 prepared using a commercial friction modifier.

TABLE II

| | Optimal SRV Friction Coefficient Test | |
|---|---|---|
| Composition | Weight Percent Additive | Friction Coefficient |
| 4 | 2 | 0.120 |
| 5 | 2 | 0.127 |
| 6 | 2 | 0.133 |
| 7 | 2 | 0.143 |
| Comparative 2 | 2 | 0.144 |

EXAMPLE 7

In this example, composition 8 was prepared according to the present invention and comprised 10W-30 oil and 2 weight percent of the beta substituted alkyl alkylene diamine prepared in Example 1. Comparative composition 3 was prepared comprising only the 10W-30 oil and comparative composition 4 was prepared comprising the 10W-30 oil and 2 weight percent of the commercial friction modifier and antiwear additive, Keil Sul Perm 307. The 10W-30 oil used in these compositions contained 1 weight percent zinc dialkyl dithiophosphate which serves as an antiwear agent and a corrosion resistant antioxidant. These compositions were subjected to the Four-Ball Wear Test according to ASTM D-4172-82 (40 Kg, 1200 rpm, 75° C., 1 hour), the results of which are set forth in Table III. These results demonstrate that the friction and wear reducing composition according to the present invention not only provides the lubricant oil with friction resistance as set forth in the previous examples, but also with wear resistance.

TABLE III

| | Four-Ball Wear Test | |
|---|---|---|
| Composition | Weight Percent Additive | Average Scar Diameter (mm) |
| 8 | 2 | 0.43 |
| Comparative 3 | — | 0.50 |
| Comparative 4 | 2 | 0.44 |

EXAMPLE 8

In this example, composition 9 according to the present invention and comparative compositions 5-9 were subjected to the Optimol Friction Coefficient Test as set forth in Example 6 except that the tests for this example were conducted at 30° C. rather than the 100° C. used in Example 6. Composition 9 according to the present invention comprised Synfluid PAO lubricant (8 cSt, supplied by Gulf) and 2 weight percent N,N-diethyl-N'-(beta-hydroxy)octadecyl ethylene diamine as a friction and wear reducing additive. Comparative composition 5 was prepared comprising the Synfluid PAO lubricant without an additional friction and wear reducing additive. Comparative compositions 6-9 were prepared comprising the Synfluid PAO lubricant and 2 weight percent of additives previously used in the art. Specifically, the additive of comparative composition 6 comprised N,N-diethyl-oleylethylene diamine, the additive of comparative composition 7 comprised N,N-dimethyl-stearyl-ethylene diamine, the additive of comparative composition 8 comprised Keil Sul Perm 307 (the sulfur containing compound supplied by Keil Chemical Division, Ferro Corporation), and the additive of comparative composition 9 comprised Amoco 6653 (supplied by Amoco Petroleum). The results of the testing are set forth in Table IV. From these results, it is observed that the compositions according to the present invention provided improved friction coefficients as compared with the comparative compositions.

TABLE IV

| Composition | Additive | Friction Coefficient |
|---|---|---|
| 9 | $C_{16}H_{33}CH(OH)CH_2NH(CH_2)_2NEt_2$ | 0.107 (avg.) |
| Comparative 5 | — | 0.136–0.196 (rough) |
| Comparative 6 | Oleyl-$NH(CH_2)_2NEt_2$ | 0.152 |
| Comparative 7 | Stearyl-$NH(CH_2)_2NMe_2$ | 0.131 |
| Comparative 8 | Keil Sul Perm 307 | 0.134 |
| Comparative 9 | Amoco 6653 | 0.131 |

The preceding examples are set forth to illustrate specific embodiments of the invention and are not intended to limit the scope of the compounds, compositions and methods of the present invention. Additional embodiments and advantages within the scope of the claimed invention will be apparent to one of ordinary skill in the art.

What is claimed is:

1. N,N-dialkyl-N'-(beta substituted) alkyl alkylene diamine of the formula

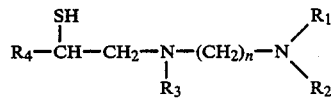

wherein $R_1$, $R_2$ and $R_3$ are $C_{1-4}$ hydrocarbon groups or H, but both $R_1$ and $R_2$ are not H, $R_4$ is a saturated or unsaturated $C_{14-24}$ hydrocarbon group, and n=1-4.

2. A friction and wear reducing composition, comprising a lubricant and a friction and wear reducing additive comprising an N,N-dialkyl-N'-(beta subsituted) alkyl alkylene diamine of the formula

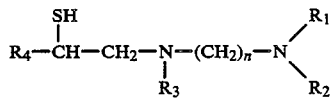

wherein $R_1$, $R_2$ and $R_3$ are $C_{1-4}$ hydrocarbon groups or H, but both $R_1$ and $R_2$ are not H, $R_4$ is a saturated or unsaturated $C_{14-24}$ hydrocarbon group, and n=1-4.

3. N,N-dialkyl-N'-(beta substituted) alkyl alkylene diamine as defined by claim 1 wherein n=1-3.

4. N,N-dialkyl-N'-(beta substituted) alkyl alkylene diamine as defined by claim 1, wherein $R_1$ and $R_2$ are $C_{1-4}$ hydrocarbon groups.

5. N,N-dialkyl-N'-(beta substituted) alkyl alkylene diamine as defined by claim 5, wherein $R_1$ and $R_2$ are the same hydrocarbon group.

6. A friction and wear reducing composition as defined by claim 2, wherein the friction and wear reducing additive is included in an amount of from about 0.1 to about 10 weight percent.

7. A friction and wear reducing composition as defined by claim 6, wherein the friction and wear reducing additive is included in an amount of from about 1 to about 5 weight percent.

8. A friction and wear reducing composition as defined by claim 2, wherein $R_1$ and $R_2$ are $C_{1-4}$ hydrocarbon groups.

9. A friction and wear reducing composition as defined by claim 8, wherein $R_1$ and $R_2$ are the same hydrocarbon group.

10. A friction and wear reducing composition as defined by claim 2, wherein the lubricant comprises a lubricating oil.

* * * * *

UNITED STATES PATENT AND TRADEMARK OFFICE
CERTIFICATE OF CORRECTION

PATENT NO. : 4,873,370

DATED : October 10, 1989

INVENTOR(S) : I-Ching Chiu

It is certified that error appears in the above-identified patent and that said Letters Patent is hereby corrected as shown below:

Column 2, lines 38-46, Table I should be deleted.

Column 3, lines 7-16, Table II should be deleted.

Signed and Sealed this

Twenty-fifth Day of September, 1990

Attest:

HARRY F. MANBECK, JR.

Attesting Officer

Commissioner of Patents and Trademarks